United States Patent [19]
Tidwell et al.

[11] Patent Number: 5,989,257
[45] Date of Patent: Nov. 23, 1999

[54] REDUNDANT SAFETY LOCK MECHANISM

[75] Inventors: Durrell G. Tidwell, Burleson; Larry D. Estes, North Richland Hills; Gary B. Gage, Arlington, all of Tex.

[73] Assignee: Midas Rex L.P., Fort Worth, Tex.

[21] Appl. No.: 09/038,613

[22] Filed: Mar. 11, 1998

[51] Int. Cl.$^6$ .................................................. A61B 17/00
[52] U.S. Cl. ................................ 606/79; 279/30; 279/75; 606/80; 606/180
[58] Field of Search ................................ 606/79, 80, 180; 279/9.1, 904, 905, 125; 81/177.85; 433/128

[56] References Cited

U.S. PATENT DOCUMENTS

| | | | |
|---|---|---|---|
| 5,464,229 | 11/1995 | Salpaka ...................................... | 279/30 |
| 5,505,737 | 4/1996 | Gosselin et al. ........................... | 606/79 |
| 5,569,256 | 10/1996 | Vaughn et al. ............................. | 606/80 |
| 5,741,263 | 4/1998 | Umber et al. .............................. | 606/80 |

*Primary Examiner*—Wynn Wood Coggins
*Assistant Examiner*—Jennifer Maynard
*Attorney, Agent, or Firm*—Senniger, Powers, Leavitt & Roedel

[57] ABSTRACT

A surgical instrument has a motor which rotates a tubular shaft about an axis. The shaft drives an implement and has an aperture which contains a ball. When the implement is installed, the ball extends through the aperture to engage the implement and lock it in. The tool has an actuation sleeve which is axially movable between locked and released positions for engaging and disengaging the ball to the implement. The actuation sleeve has an axial slot and a safety sleeve located radially outward from the actuation sleeve. The safety sleeve has a pin which extends radially inward and a cylinder extending radially outward. The cylinder contains a ball which is biased inward. The outer surface of the tool has a pair of detents for receiving the ball. The safety sleeve has locked and unlocked positions. In the unlocked position, the pin is aligned with the slot and the ball engages the first detent to permit the actuation sleeve to move between the locked and released positions. In the locked position, the safety sleeve is rotated so that the pin is misaligned with the slot and the ball engages the second detent to prevent the actuation sleeve from moving to the released position.

20 Claims, 2 Drawing Sheets

REDUNDANT SAFETY LOCK MECHANISM

TECHNICAL FIELD

This invention relates in general to surgical instruments for use in the dissection of bone and other tissue, and in particular to a safety lock mechanism for a quick release collet on a motorized surgical instrument.

BACKGROUND ART

Surgical instruments that utilize high speed rotary motors with shafted implements for the resection of bone and tissue are common in the art. One type of surgical instrument has a quick release mechanism that can engage and disengage the tool implement. When a surgical implement needs to be changed or replaced, an actuating sleeve is moved to a released position to remove the implement. The new implement is then inserted and the actuating sleeve is moved back to a locked position.

DISCLOSURE OF THE INVENTION

A surgical instrument for the resection of tissue has a motor which rotates a tubular shaft about an axis. The shaft drives a surgical tool implement. The shaft has an aperture which contains a ball. When the implement is installed, the ball extends through the aperture to engage a recess in the implement to lock it in the surgical instrument.

The tool has an actuation sleeve which is axially movable between locked and released positions for engaging and disengaging the ball to the recess. The actuation sleeve has an axial slot which extends from its rearward end. The tool also has a safety sleeve located radially outward from the actuation sleeve. The safety sleeve has a pin which extends radially inward and a cylinder extending radially outward. The cylinder contains a ball which is biased radially inward. The outer surface of the tool has a pair of detents for receiving the ball. The safety sleeve has locked and unlocked positions. In the unlocked position, the pin is aligned with the actuation sleeve slot, and the ball engages one of the detents to permit the actuation sleeve to move between the locked and released positions. In the locked position, the safety sleeve is rotated so that the pin is misaligned with the slot, and the ball engages the other detent to prevent the actuation sleeve from moving to the released position.

BEST MODE FOR CARRYING OUT THE INVENTION

Figure 1:
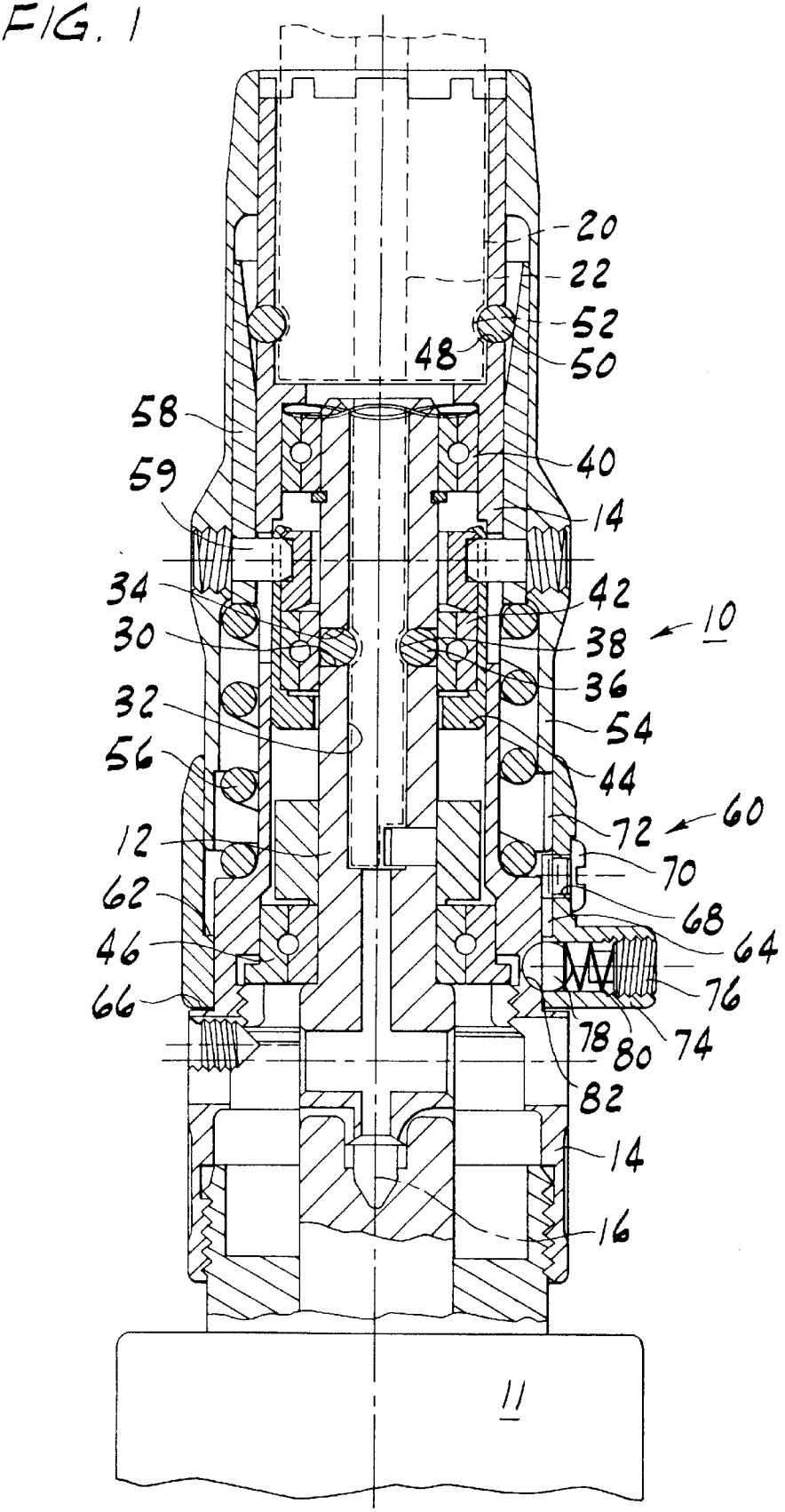
FIG. 1 is a sectional side view of a surgical instrument constructed in accordance with the invention and having a safety mechanism for a slidable actuation sleeve with the safety mechanism in the unlocked position and the actuation sleeve in the locked position.

Referring to FIG. 1, a surgical instrument 10 used for the resection of tissue in surgical procedures is shown. Instrument 10 is provided with a fluid driven motor 11 having an air conduit (not shown) which provides a source of pressurized air to the motor. The motor drives a tubular shaft 12 inside a housing 14. Housing 14 has internal threads for engaging a drive motor (not shown). Shaft 12 is rotated by the motor about a longitudinal axis 16. A guide tube 20 (indicated by dashed lines) extends from and is joined at the forward end of instrument 10. Guide tube 20 supports a cutting tool implement 22 (also indicated by dashed lines) on its forward end. Shaft 12 is used to transmit torque from the motor to implement 22.

Shaft 12 has a plurality of circular apertures 30 near its axial midpoint which extend radially outward from a central bore 32. Each aperture 30 decreases in diameter towards central bore 32 to form a conical locking member seat 34. Spherical locking members or balls 36 fit within apertures 30 and engage an annular recess 38 (indicated by dashed lines) in implement 22. Prior to the installation of implement 22, balls 36 are free to roll or move within apertures 30, but are prevented from fully entering central bore 32 by locking member seats 34 located at the inner edge of apertures 30. Once implement 22 is installed, balls 36 engage recess 38 and prevent the axial movement of implement 22.

Shaft 12 rotates within tool 10 on three roller bearings. A first bearing 40 is located at the forward end of shaft 12. A second bearing 42 is located between apertures 30 and a boss 44 on the inner surface of housing 14. A third bearing 46 is located between the rearward end of shaft 12 and housing 14. Thus, shaft 12, locking members 36, implement 22 and the inner races of each bearing all rotate within housing 14.

Housing 14 has two opposing circular apertures 48 forward of first bearing 40. Spherical locking members or balls 50 fit within apertures 48 and extend into an annular recess 52 (indicated by dashed lines) on sleeve 20. Balls 50 operate with apertures 48 in exactly the same way as balls 36 operate with apertures 30. Balls 50 prevent the axial movement of sleeve 20 when it is installed in tool 10.

Tool 10 has a quick release mechanism that can lock or release both implement 22 and sleeve 20 simultaneously. Encircling housing 14 is a cylindrical actuating sleeve 54. The radial inner surface of actuating sleeve 54 closely receives a forward portion of housing 14 so that actuating sleeve 54 slides along the exterior of housing 14 for a short distance when moved between locked and released positions along lines parallel to axis 16. A coiled spring 56 is located between housing 14 and actuating sleeve 54. The rearward end of spring 56 abuts housing 14 while the forward end of spring 56 abuts a rearward end of a cam sleeve 58. Cam sleeve 58 is located adjacent to first bearing 40 and slidingly receives the forward end of housing 14. Spring 56 is axially biased to urge cam sleeve 58 forward. Cam sleeve 58 is attached to actuating sleeve 54 and boss 44 with screws 59 which extend through holes in each member such that cam sleeve 58, actuating sleeve 54 and boss 44 move integrally and slidingly together.

A generally cylindrical safety mechanism or sleeve 60 is located radially outward from actuating sleeve 54 near the rearward end of tool 10. A forward portion of the inner surface of sleeve 60 slidingly receives a rearward portion of the outer surface of actuating sleeve 54. Sleeve 60 has a small shoulder 62 on an inner wall which creates a small annular space 64 between sleeve 60 and the outer surface of housing 14. A rearward edge of sleeve 60 abuts a shoulder 66 on housing 14.

Figure 2:
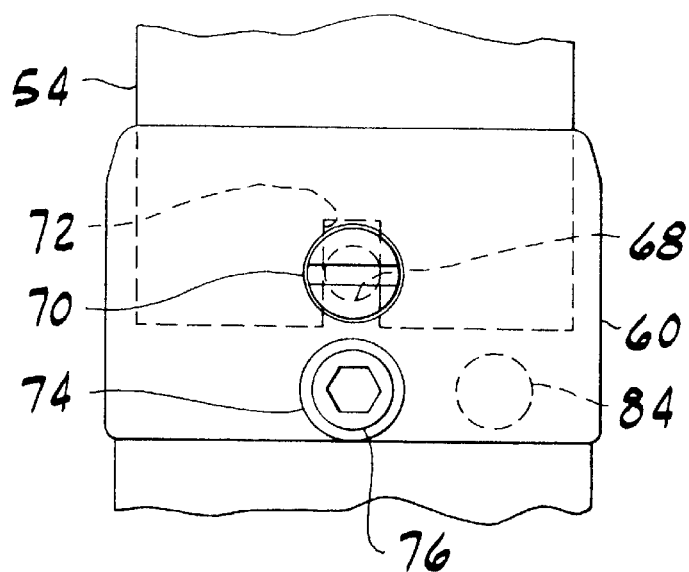
FIG. 2 is a partial top view of the surgical instrument of FIG. 1 with the safety mechanism in the unlocked position and the actuation sleeve in the released position.
Figure 3:
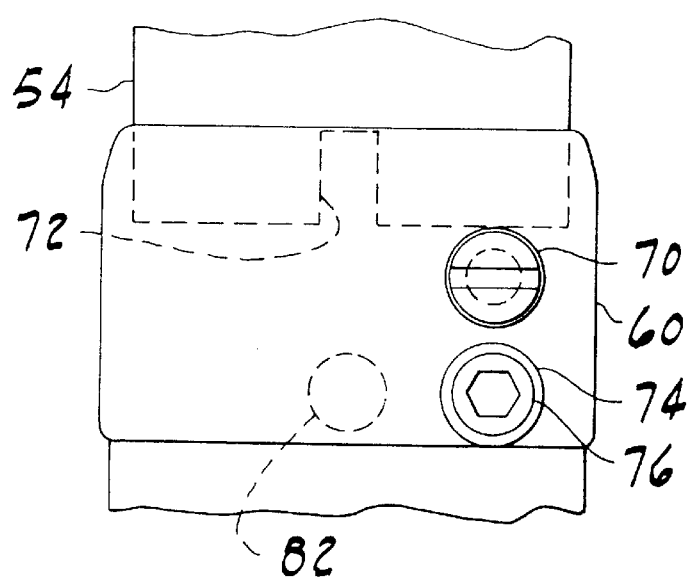
FIG. 3 is a top view of the surgical instrument of FIG. 1 with the safety lock in the locked position and the actuation sleeve in the locked position.

As shown in FIGS. 1–3, sleeve 60 has a threaded hole 68 with a short screw or pin 70 extending radially inward therethrough. Screw 70 has a length which is approximately equal to the thickness of sleeve 60 and the width of space 64 so that it does not engage the outer surface of housing 14 when it is fully threaded into sleeve 60. An axial slot 72 extends from the rearward end of actuating sleeve 54 forward for a short distance. Slot 72 has a width which is slightly greater than the diameter of the shaft of pin 70.

Sleeve 60 also has an integrally formed hollow cylinder 74 extending radially outward from a rearward end. Cylinder 74 has a threaded outer portion containing a set screw 76 and a smooth inner portion containing a ball 78. Ball 78 is slightly smaller in diameter than the smooth inner portion of cylinder 74. A compression spring 80 is located between screw 76 and ball 78 for biasing ball 78 radially inward against housing 14. Housing 14 has a pair of hemispherical detents 82, 84 (FIGS. 2 and 3) located adjacent to shoulder 66 for receiving a radially inner portion of ball 78. Detents 82, 84 are circumferentially spaced-apart from each other on the outer surface of housing 14.

Sleeve 60 has two positions: an unlocked position wherein pin 70 is axially aligned with slot 72 (FIG. 2) and a released position in which pin 70 is out of alignment with slot 72 (FIG. 3). While pin 70 is in the unlocked position, it will permit actuating sleeve 54 to move between its locked (FIG. 1) and released positions (FIG. 3) While pin 70 is in the locked position, the rear edge of actuating sleeve 54 will abut pin 70 and cannot move rearward to its released position. Detent 82 and ball 78 releasably retain sleeve 60 in the unlocked position and detent 84 retains sleeve 60 in the locked position. To move the safety device from the unlocked to the locked positions, sleeve 60 is rotated so that pin 70 is misaligned with slot 72 and abuts a rearward end of actuating sleeve 54.

To install a new cutting tool implement 22, sleeve 60 is placed in the unlocked position so that actuating sleeve 54 may slide rearward toward sleeve 60, moving from its locked position to the released position. Two events occur simultaneously when actuating sleeve 54 slides rearward. Cam sleeve 58 is tapered on its forward end such that when it moves rearward with actuating sleeve 54, it permits balls 50 to move freely away from recess 52 of sleeve 20 so that sleeve 20 may be removed. At the same time, second bearing 42 slides rearward, allowing balls 36 to move radially outward and away from recess 38 of implement 22 so that implement 22 may be removed. After implement 22 is installed, actuating sleeve 54 springs forward to the locked position, and sleeve 60 is manually rotated to the locked position by the user's finger. Tool 10 is ready for use when sleeve 60 in the locked position.

The invention has advantages. The locking sleeve described above is provided as a redundant safety mechanism for preventing a user from accidentally or unintentionally moving the actuating sleeve to the disengaged position.

While the invention has been shown or described in only some of its forms, it should be apparent to those skilled in the art that it is not so limited, but is susceptible to various changes without departing from the scope of the invention. For example, the slot could be located in the safety sleeve and the pin could be located on the actuating sleeve. The detents and ball positions could also be reversed.

I claim:

1. A surgical instrument having a forward end from which a tool implement projects an axis and connectable to a motor, comprising:

a housing having forward and rearward ends;

a tubular shaft located within the housing and having a bore for selectively receiving a tool implement therein, the shaft aligning with the axis and being rotated by the motor;

a lock member movably carried by the shaft and having a locked position which locks a tool implement to the shaft and a released position which releases a tool implement, thereby allowing a tool implement to be withdrawn from the bore of the shaft;

an actuation sleeve surrounding the shaft, the actuation sleeve being movable between a locked position for placing the lock member in the locked position, and a released position for placing the lock member in the released position; and a safety mechanism including a coaxial safety sleeve which is movable relative to the actuation sleeve between an unlocked position wherein the actuation sleeve is free to move between the locked and released positions, and a locked position wherein the actuation sleeve is obstructed from moving to the released position and means cooperating with the safety sleeve and the actuation sleeve to releasably retain the actuation sleeve in its locked position.

2. The surgical instrument of claim 1 wherein the actuation sleeve moves axially between its locked and released positions, and the safety sleeve moves rotationally between its locked and unlocked positions.

3. The surgical instrument of claim 1 wherein:

the actuation sleeve moves axially between its locked and released positions;

one of the actuation sleeve and the safety sleeve has an axially extending slot and a shoulder; and the other of the actuation sleeve and the safety sleeve has a radially extending pin, the safety sleeve being rotatable relative to the actuation sleeve between its unlocked position, wherein the pin is aligned with the slot as the actuation sleeve moves between its locked and released positions, and its locked position, wherein the pin is misaligned with the slot and abuts the shoulder for preventing the actuation sleeve from moving to its released position.

4. The surgical instrument of claim 1, further comprising means for releasably retaining the safety sleeve in its locked position.

5. The surgical instrument of claim 2, further comprising:
   a detent; and
   a radially biased ball mounted on the safety sleeve and selectively engageable with the detent to releasably retain the safety sleeve in its locked position when said radially biased ball is engaged in said detent.

6. The surgical instrument of claim 2, further comprising:
   a pair of detents; and
   a radially biased ball mounted on the safety sleeve and selectively engageable with the detents to releasably retain the safety sleeve in its locked and unlocked positions when said radially biased ball is selectively engaged with said detents.

7. The surgical instrument of claim 6 wherein the radially biased ball is located within a cylinder which extends radially outward from the safety sleeve and wherein the radially biased ball is biased radially inward by a spring located within the cylinder.

8. The surgical instrument of claim 7 wherein the cylinder has a set screw threaded into an outer portion and wherein the spring is located between the set screw and the ball.

9. The surgical instrument of claim 1 wherein the safety mechanism is located axially rearward and radially outward of the actuation sleeve.

10. The surgical instrument of claim 1 wherein an inner surface of the safety sleeve slidingly engages an outer surface of the actuation sleeve.

11. A surgical instrument having an axis, the surgical instrument comprising:

a housing having forward and rearward ends;

a motor mounted on the housing adjacent the rearward end;

a tool implement having a recess spaced from one end;

a tubular shaft having a bore and an aperture and being located within the housing for receiving the tool implement in the bore adjacent the forward end, the shaft aligning with the axis and being rotated by the motor;

a locking element which moves radially inward into the aperture to engage the recess on the tool implement in a locking position, and which moves radially outward out of the aperture and the recess to a released position wherein the tool implement may be disengaged from the tubular shaft;

an actuation sleeve surrounding the shaft and operably associated with the locking element, the actuation sleeve being axially movable between locked and released positions to permit movement of the locking element between its locked and released positions;

a coaxial safety sleeve which is rotatable between locked and unlocked positions relative to the actuation sleeve; and a pin secured to the actuation sleeve or the safety sleeve and a mating slot in the other of the actuation sleeve and safety sleeve, whereby, when the actuation sleeve is in its unlocked position, the pin registers with the slot to allow the actuation sleeve to move axially between its locked and released positions, and when the safety sleeve is in its locked position, the pin is misaligned with the slot for preventing the actuation sleeve from moving from its locked position.

12. The surgical instrument of claim 11 wherein the slot is in the actuation sleeve and the pin is secured to the safety sleeve.

13. The surgical instrument of claim 11, further comprising a protuberance extending from an outer surface of the safety sleeve for engagement by a finger of a user to rotate the safety sleeve.

14. The surgical instrument of claim 11, further comprising:

a radially inward biased ball projecting inwardly from an internal surface of the safety sleeve; and a detent located on a surface of the surgical instrument which receives the safety sleeve for selective engagement by the radially inward biased ball to releasably retain the safety sleeve in its locked position.

15. The surgical instrument of claim 11, further comprising:

a radially inward biased ball projecting inwardly from an internal surface of the safety sleeve; and a pair of detents located on a surface of the surgical instrument which receives the safety sleeve for selective engagement by the radially inward biased ball to releasably retain the safety sleeve in its locked and unlocked positions.

16. The surgical instrument of claim 15 wherein the radially inward biased ball is located within a cylinder which extends radially outward from the safety sleeve and wherein the radially inward biased ball is biased radially inward by a spring located within the cylinder.

17. The surgical instrument of claim 16 wherein the cylinder has a set screw threaded into an outer portion and wherein the spring is located between the set screw and the radially inward biased ball.

18. The surgical instrument of claim 11 wherein the safety sleeve is located axially rearward and radially outward of the actuation sleeve.

19. The surgical instrument of claim 11 wherein an inner surface of the safety sleeve slidingly engages an outer surface of the actuation sleeve.

20. A surgical instrument having an axis and a motor, comprising:

a housing having forward and rearward ends;

a motor mounted on the housing adjacent the rearward end;

a tool implement having a recess spaced from one end;

a tubular shaft having a bore and an aperture and being located within the housing for receiving the tool implement at the forward end, the shaft aligning with the axis and being rotated by the motor;

a locking element which moves radially inward into the aperture to engage the recess on the tool implement in a locking position, and which moves radially outward out of the aperture to a released position wherein the tool implement may be disengaged from the tubular shaft;

an actuation sleeve surrounding the shaft and operatively associated with the locking element, the actuation sleeve being axially movable between locked and released positions to permit movement of the locking element between its locked and released positions;

a coaxial safety sleeve which is rotatable between locked and unlocked positions relative to the actuation sleeve, the safety sleeve being located axially rearward and radially outward of the actuation sleeve;

a pin secured to the safety sleeve and a mating slot in the actuation sleeve, whereby, when the safety sleeve is in its unlocked position, the pin registers with the slot to allow the actuation sleeve to move axially between its locked and released positions, and when the safety sleeve is in its locked position, the pin is misaligned with the slot for preventing the actuation sleeve from moving from its locked position;

a ball and detent operatively associated with the safety sleeve to releasably retain the safety sleeve in its locked position.

* * * * *